United States Patent [19]

Wang et al.

[11] Patent Number: 6,074,642

[45] Date of Patent: *Jun. 13, 2000

[54] USE OF ANTIBODIES SPECIFIC TO HUMAN COMPLEMENT COMPONENT C5 FOR THE TREATMENT OF GLOMERULONEPHRITIS

[75] Inventors: Yi Wang, Orange; Louis Matis, Southport; Scott Rollins, Monroe, all of Conn.

[73] Assignee: Alexion Pharmaceuticals, Inc., New Haven, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/236,208

[22] Filed: May 2, 1994

[51] Int. Cl.7 .................................................. A61K 39/395
[52] U.S. Cl. ..................... 424/145.1; 424/130.1; 424/140.1; 424/141.1; 424/152.1; 424/158.1
[58] Field of Search ............................ 424/130.1, 140.1, 424/141.1, 145.1, 152.1, 158.1; 530/387.1, 388.1, 388.23, 388.25, 389.3, 380

[56] References Cited

U.S. PATENT DOCUMENTS

| | | |
|---|---|---|
| 4,686,100 | 8/1987 | Raffin et al. . |
| 5,135,916 | 8/1992 | Sims . |
| 5,173,499 | 12/1992 | Sindelar et al. . |
| 5,506,247 | 4/1996 | Sindelar et al. . |
| 5,635,178 | 6/1997 | Sims et al. . |

*Primary Examiner*—Lila Feisse
*Assistant Examiner*—Phillip Gambel
*Attorney, Agent, or Firm*—Seth A. Fidel; Maurice M. Klee

[57] ABSTRACT

The use of anti-C5 antibodies, e.g., monoclonal antibodies, to treat glomerulonephritis (GN) is disclosed. The administration of such antibodies at low dosage levels has been found to significantly reduce glomerular inflammation/enlargement and other pathologic conditions associated with GN.

5 Claims, 7 Drawing Sheets

USE OF ANTIBODIES SPECIFIC TO HUMAN COMPLEMENT COMPONENT C5 FOR THE TREATMENT OF GLOMERULONEPHRITIS

FIELD OF THE INVENTION

The present invention relates to the treatment of glomerulonephritis (GN). In particular, the invention relates to the use of antibodies specific to human complement component C5 to accomplish such therapeutic treatment.

BACKGROUND OF THE INVENTION

I. Immune Complex Mediated Disease

The formation of immune complexes is the typical consequence of the interaction of antigens with specific antibodies. The inflammatory response that ensues when such complexes accumulate in a limited area is an important element of normal host defenses, leading to immune complex clearance and antigen destruction by phagocytic cells. In contrast, immune complex diseases are reflections of excess complex formation or retarded clearance, usually under conditions of exceptional antigen challenge or immunologic dysregulation. Under such circumstances, immune complexes are deposited or formed at specific tissue sites and resulting inflammatory responses lead to disease states due to localized or systemic tissue damage. The kidney, and more specifically the kidney structure known as the glomerulus, is a particularly important site of immune complex deposition resulting in the development of serious disease conditions.

II. Glomerulonephritis

The glomerulus is a key structural and functional element of the kidney. Each glomerulus is found as part of a larger structure that serves as the main functional unit of the kidney and is called a nephron. About a million nephrons are found in each kidney. Each glomerulus is a network of up to fifty parallel capillaries encased in a structure known as Bowman's capsule. The area inside Bowman's capsule that is not taken up by the glomerular capillaries is known as Bowman's space. The glomerulus functions as a filter, separating water and certain solutes from the proteins and cells of the blood into Bowman's space for further processing in the convoluted tubules, loop of Henle, and collecting duct of the nephron.

Glomerulonephritis (GN) is a disease of the kidney characterized by inflammation and resulting enlargement of the glomeruli that is typically due to immune complex formation. The accumulation of immune complexes in the glomeruli results in inflammatory responses, involving inter alia hypercellularity, that can cause total or partial blockage of the glomerulus through, among other factors, narrowing of capillary lumens. One result of this process is the inhibition of the normal filtration function of the glomerulus. Blockage may occur in large numbers of glomeruli, directly compromising kidney function and often causing the abnormal deposition of proteins in the walls of the capillaries making up the glomerulus. Such deposition can, in turn, cause damage to glomerular basement membranes. Those glomeruli that are not blocked develop increased permeability, allowing large amounts of protein to pass into the urine, a condition referred to as proteinuria.

In many cases of severe GN, pathological structures called crescents are formed within the Bowman's space, further impeding glomerular filtration. These structures can only be seen by microscopic examination of tissue samples obtained by biopsy or necropsy, and are thus not always observed in those patients in which they occur. Crescents are a manifestation of hypercellularity and are thought to arise from the extensive abnormal proliferation of parietal epithelial cells, the cells that form the inner lining of the Bowman's capsule. Clinical research has shown that there is a rough correlation between the percentage of glomeruli with crescents and the clinical severity of the disease, and thus the patient's prognosis. When present in large numbers, crescents are a poor prognostic sign.

Symptoms of GN include: proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria.

In 1990, over 210,000 patients in the United States required hemodialysis or transplantation for chronic renal failure at an annual cost in excess of 7 billion dollars, according to the United States Renal Data System (USRDS). The USRDS compiles data on kidney disease in the United States in conjunction with the National Institute of Diabetes and Digestive and Kidney Diseases, Division of Kidney, Urologic, and Hematologic Diseases, of the National Institutes of Health (NIDDKD). The USRDS estimates that the costs of treatment for renal failure are now increasing by 20 percent annually.

GN is the third leading cause of death in end-stage renal disease patients, exceeded only by diabetes and hypertension. As a result, there is a clear and long felt need in the medical community for effective treatments for this condition. Research aimed at the development of new treatments for GN is ongoing worldwide. In the United States, the NIDDKD, the National Kidney Foundation, and several other public and private organizations sponsor research in this area. The National Kidney Foundation alone supplies over two million dollars annually to fund the efforts of kidney researchers.

III. Current Treatments for GN

Corticosteroid administration, typically as high doses of "pulse" intravenous methylprednisolone or oral prednisone therapy, is currently considered the most effective pharmacologic agent available for the treatment of GN. Such steroid therapy is often administered in combination with cytotoxic general immunosuppressive agents such as azathioprine or cyclophosphamide. The overall immune suppression and resulting increased susceptibility to infection, along with other debilitating side effects associated with both steroid and cytotoxic drug administration, limit the effective use of these drugs.

Aspirin-like non-steroidal anti-inflammatory drugs (NSAIDs) have also been used to reduce the glomerular inflammation and enlargement of GN. These drugs are not routinely used for this purpose, however, probably because of their relatively weak anti-inflammatory effects and propensity to cause gastrointestinal and other side effects in many patients.

The administration of anticoagulants such as heparin or warfarin sodium, and antithrombotic agents such as cyproheptadine, dipyridamole, or sulfinpyrazone, has been used on the basis of evidence suggesting the involvement of the coagulation process in the genesis of glomerular crescents. However, objective evidence of benefit from such therapies in animals afflicted with experimentally induced crescentic GN has been inconsistent. Also, anticoagulants are dangerous drugs, as they can potentiate life-threatening bleeding episodes. They are especially hazardous in this regard in patients with advanced renal failure.

In addition to pharmacologic approaches, intensive plasma exchange (plasmapheresis) of 2 to 4 liters of plasma daily (or in some cases three times a week) can dramatically reduce high levels of circulating immune complexes when acute intervention in the inflammatory process is needed. Such treatment is expensive and requires that the patient be connected to the plasmapheresis machine for many hours each week. In addition, all procedures in which blood is removed from and returned to a patient are associated with an increased risk of infection. Nonetheless, plasma exchange is currently considered the most effective non-pharmacological treatment for removal of circulating immune complexes which can cause GN.

Circulating immune complex levels can also be decreased by eliminating or reducing the source of the antigen or antigens contained in the complexes by, for example, effective therapy of an underlying infection or change in an antibiotic. However, while such therapy is almost always a treatment of choice, great care must be taken since reduction of the antigen load alters the molar ratio of antigen to antibody involved in forming immune complexes and thus a dangerous temporary exacerbation of the inflammatory process may occur (see discussion below in Background Physiology & Pathology).

SUMMARY OF THE INVENTION

In view of the foregoing, it is an object of the present invention to provide a new approach for reducing the glomerular inflammation and kidney dysfunction associated with GN.

The method of the invention involves the use of preparations containing antibodies to human complement component C5 as pharmaceutical agents. More particularly, the invention provides for the use of anti-C5 antibodies that bind to complement component C5 or active fragments thereof. Preferably, the antibodies block the generation and/or activity of complement components C5a and C5b. For most applications, the antibody is a monoclonal antibody.

In the preferred embodiments of the invention, the administration of the anti-C5 antibody preparation is started after the appearance of GN symptoms, e.g., after the appearance of proteinuria. Alternatively, the invention can be used prophylactically to treat patients who are at risk for an acute exacerbation of existing GN, e.g., patients experiencing a flare-up of symptoms of systemic lupus erythematosus or similar autoimmune diseases that have resulted in GN.

As shown in the examples presented below, anti-C5 antibodies administered subsequent to the onset of GN essentially eliminate glomerular inflammation/enlargement and reduce kidney dysfunction (see Examples 1 and 2).

Although not wishing to be bound by any particular theory of operation, it is believed that the anti-C5 antibodies have these therapeutic effects through their activity in blocking the generation or activity of the C5a and/or C5b active fragments of complement component C5. Through this blocking effect, the antibodies inhibit the proinflammatory (anaphylatoxic) effects of C5a and the generation of the C5b-9 membrane attack complex (MAC). Significantly, the blockage effected by the anti-C5 antibodies, since it occurs at the level of complement component C5, has the advantage of maintaining important opsonic, anti-infective, and immune complex clearance functions of the complement system mediated by, inter alia, complement component C3.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

BRIEF DESCRIPTION OF THE DRAWINGS

FIG. 1A—uninduced untreated mouse. FIG. 1B—GN-induced PBS-(control)-treated mouse. FIG. 1C—GN-induced anti-C5 treated mouse. Magnification for each is the same, approximately 400×.

FIG. 2A—uninduced untreated mouse. FIG. 2B—GN-induced PBS-(control)-treated mouse. FIG. 2C—GN-induced anti-C5 treated mouse. Magnification for each is the same, approximately 200×.

FIG. 5A—uninduced untreated mouse. FIG. 5B—GN-induced PBS-(control)-treated mouse. FIG. 5C—GN-induced anti-C5 treated mouse. Magnification for each is the same, approximately 400×.

Figure 1A:
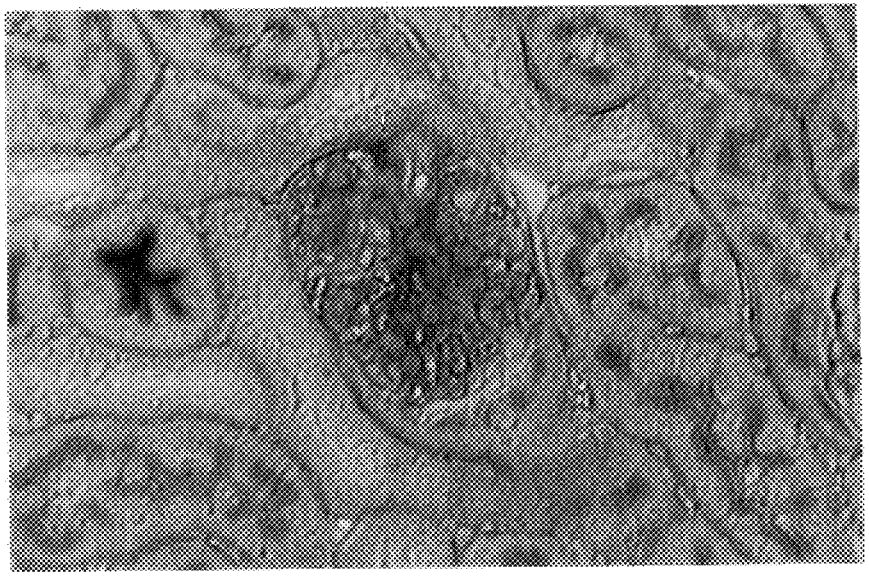
FIGS. 1A, 1B, and 1C—Photomicrographs of PAS stained sections of mouse kidneys.
Figure 1B:
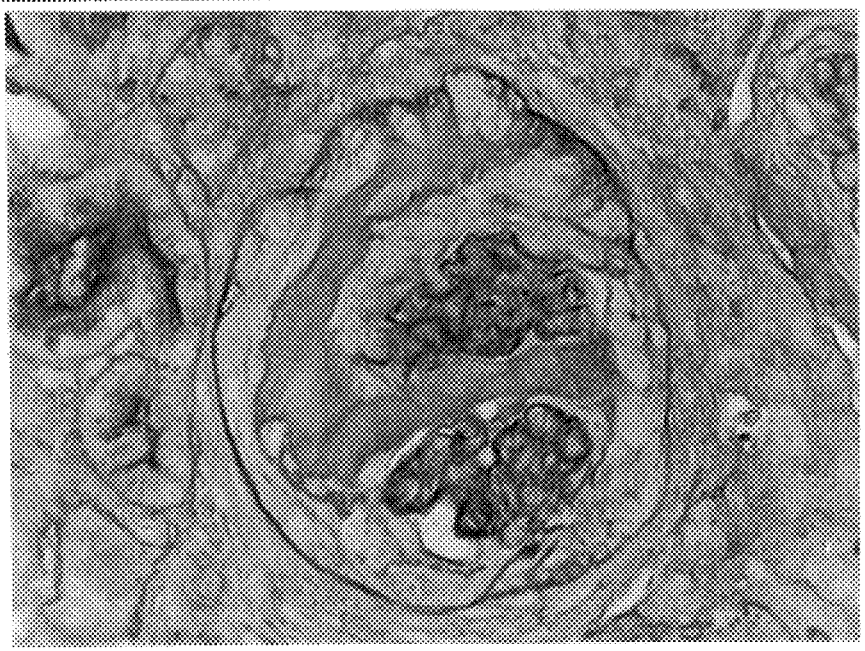
Figure 2A:
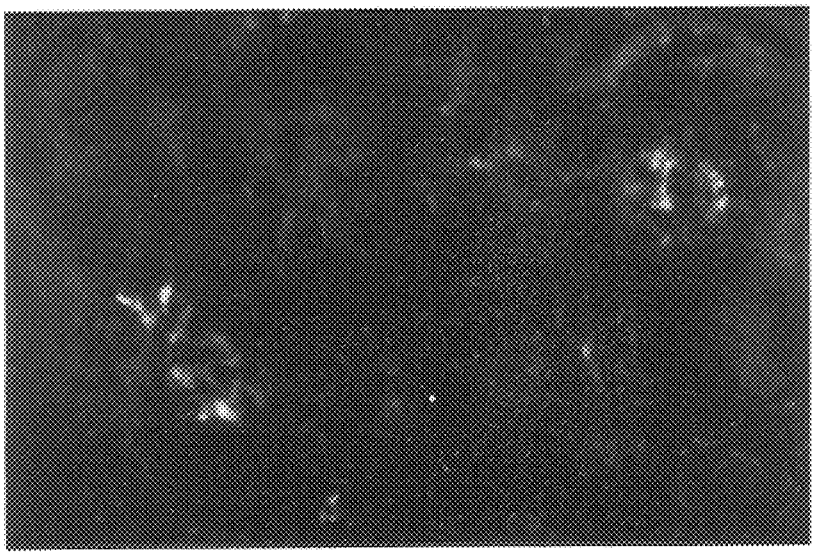
FIGS. 2A, 2B, and 2C—Photomicrographs of immunofluorescence stained sections of mouse kidneys.
Figure 2B:
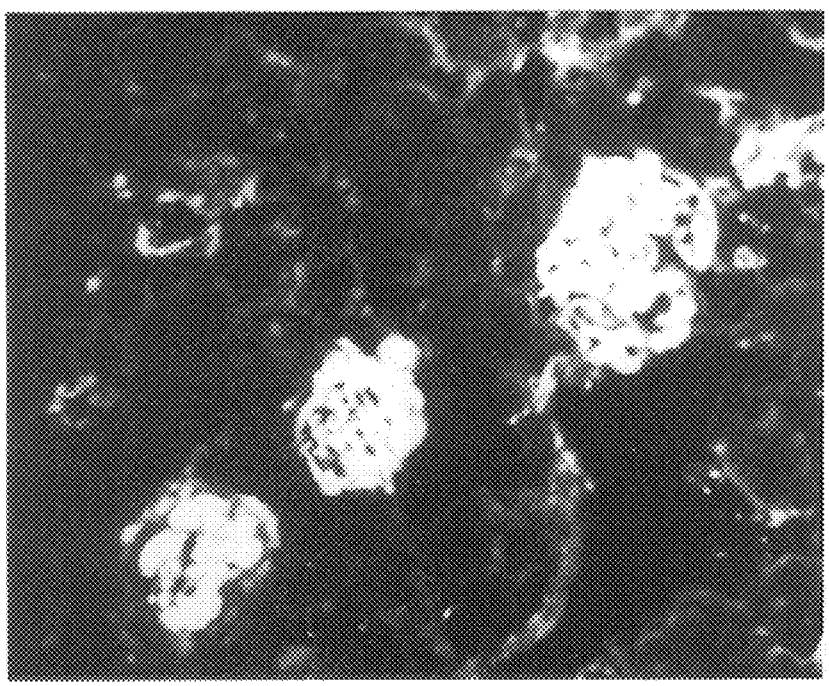
Figure 5A:
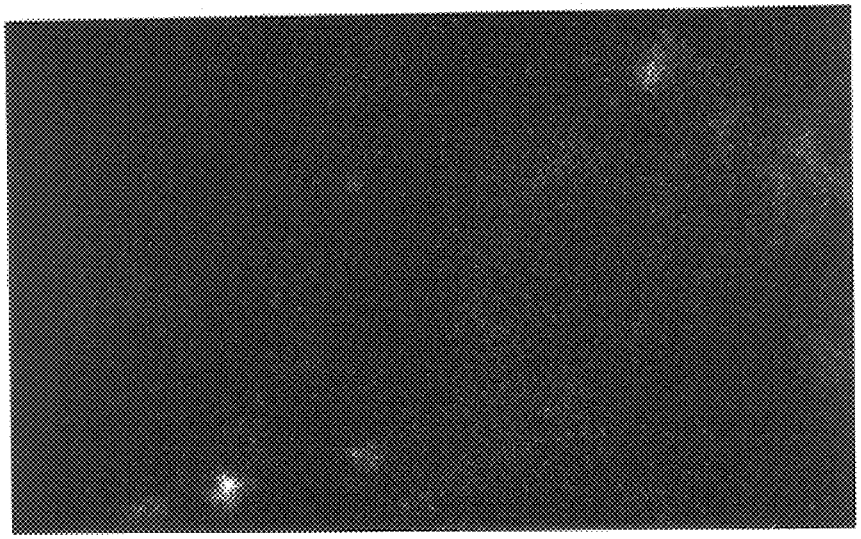
FIGS. 5A, 5B, and 5C—Immunofluorescence photomicrographs of kidney sections stained for mouse C3.
Figure 5B:
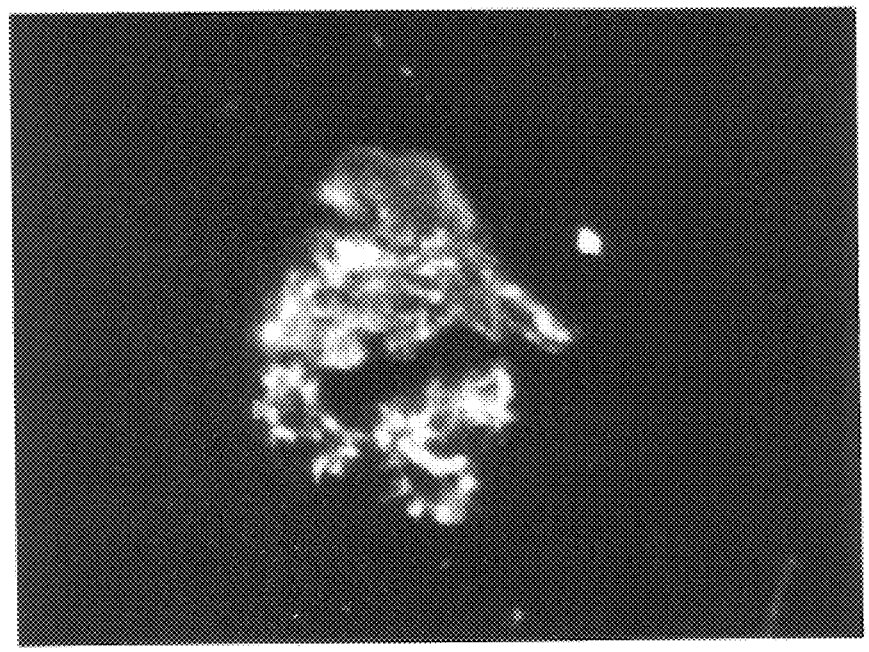

The immunofluorescent staining of FIGS. 2 and 5 is confined to the glomerular capillary network (tuft) and thus the enlargement of the glomerulus seen in FIG. 1B is not visible in FIGS. 2B and 5B.

BACKGROUND PHYSIOLOGY & PATHOLOGY

I. Introduction

As described above, the present invention relates to therapeutic treatments for GN. To provide background for the description of the preferred embodiments and the examples presented below, we turn first to general discussions of the complement arm of the immune system, the pathophysiologic features of GN, and previous studies of the role of complement in GN pathogenesis.

General discussions of the complement system and GN can be found in, for example, Glassock and Brenner, 1994; Couser, 1993; Couser, 1992; Couser, et al, 1992; Rich, 1992; Glassock and Brenner, 1987; Robbins and Cotran, 1979; and Guyton, 1971.

II. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and while they differ in their initial steps, they converge and share the same "terminal complement" components (C5 through C9) responsible for the activation and destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin (see discussion below). C3b binds to bacterial and other cells, as well as to certain viruses and immune complexes, and tags them for removal from the circulation. (C3b in this role is known as opsonin.) The opsonic function of C3b is considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to Neisseria infection, and then only somewhat more prone (Fearon, in *Intensive Review of Internal Medicine,* 2nd Ed. Fanta and Minaker, eds. Brigham and Women's and Beth Israel Hospitals, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner, et al., *Complement Inflamm.* 8:328–340, 1991). This property of C3b is regulated by the serum protease Factor I, which acts on C3b to produce iC3b. While still functional as opsonin, iC3b cannot form an active C5 convertase.

C5a is another anaphylatoxin (see discussion below). C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

III. Pathophysiology of GN

Although GN may accompany an extraordinary range of pathologic processes, in general it is encountered most commonly in the course of infectious diseases, in autoimmunity, and as a consequence of therapy for some other disease process. The causative mechanism for GN is typically the deposit of circulating immune complexes in the kidney. Factors involved in the pathogenesis of GN include the specific antigen and antibody involved and the inflammatory processes that occur as a consequence of immune complex deposition.

Antigens Involved in the Formation of Immune Comolexes that Cause GN

Antigens involved in the development of GN can be broadly classified as endogenous, infectious, and iatrogenic (those encountered as a consequence of medical practice). In many cases the specific antigen is unknown, although the general class can usually be identified.

The best known example of the formation of endogenous immune complexes is the DNA anti-DNA complexes produced in connection with systemic lupus erythematosus (lupus, SLE). Other important sources of endogenous antigens include malignancies in which immune complex formation may contribute to the development of paraneoplastic syndromes.

Infections with organisms of many types, particularly chronic infections, are also associated with the development of immune complexes that can cause GN. Bacterial and fungal infections that can produce such complexes include infection with certain strains of streptococci, Pseudomonas, disseminated gonococcal infection, lepromatous leprosy, subacute bacterial endocarditis, bronchopulmonary aspergillosis, secondary syphilis, and chronic infections in patients with cystic fibrosis.

Viral diseases in which immune complex deposition may be a prominent feature include hepatitis B infection, dengue, infectious mononucleosis, and subacute sclerosing panencephalitis. GN is also a prominent feature of many parasitic infestations such as the GN seen in children with quartan malaria, as well as toxoplasmosis, trypanosomiasis, and schistosomiasis.

Iatrogenic antigens constitute a special class of exogenous antigens. These include those responsible for the prototype immune complex disease, serum sickness, which follows formation of immune complexes between heterologous serum constituents and autologous antibodies. Serum sickness was regularly seen earlier in this century when infectious diseases were frequently treated with heterologous antisera.

An iatrogenic disease essentially indistinguishable from classic serum sickness can occur as a consequence of high-dose antibiotic therapy. The serum sickness-like manifestations of immune responses to these drugs include GN and reflect the fact that certain drugs, particularly the β-lactam and sulfonamide antibiotics, are effective haptens that are capable of inducing antibody responses upon spontaneous conjugation to autologous proteins.

Factors Affecting Immune Complex Formation and Deposition

Features of both antigen and antibody determine the likelihood of pathologic immune complex formation and subsequent deposition in the kidney. Chief among these are the absolute concentrations of the reactants and their relative molar ratios.

Most antigens display multiple epitopes and typically stimulate a polyclonal antibody response. All naturally occurring antibody molecules are at least bivalent. These properties allow for the formation of an extensive antigen-antibody lattice, the size of which is determined largely by the affinity of the antibodies and the molar ratio of antigen to antibody.

In general, antibody responses begin under conditions in which antigen is present in excess to antibody, and this relative ratio changes as the antibody response increases in magnitude. Complexes formed initially are usually small and exhibit little or no pathogenic activity. In contrast, very large complexes are often formed as the amount of antigen becomes limiting, late in the course of an antibody response under conditions of antibody excess. Because these very large complexes are readily cleared by the reticuloendothelial system in the liver, they are also relatively nonpathogenic.

The formation of immune complexes that can cause GN is believed to occur during conditions of slight antigen excess or near the point of antibody-antigen equivalence, where lattice formation is maximal and lattice size is large, but not very large.

Several factors influence the speed and location of immune complex precipitation. Interactions between Fc regions of antibody molecules promote rapid precipitation of immune complexes. The role of Fc—Fc interactions in immune complex precipitation is illustrated by studies of the properties of F(ab')2 antibody fragments, which do not contain Fc regions. Although the valence of F(ab')2 fragments does not differ from that of most whole immunoglobulins, F(ab')2 antibody fragments form lattices more slowly.

Antigen charge plays a role in determining the tissue localization of sites of deposition of immune complex precipitates. Complexes with a substantial positive charge are preferentially attracted to the strong negative charge of basement membranes, particularly in the renal glomerulus.

Localized presence of antigen may largely account for certain cases of organ specific immune complex deposition. Diseases such as Goodpasture's syndrome (a rare form of GN) are typically not classified as immune complex diseases because the complexes are formed in situ in the kidney rather than being preformed in the circulation and then deposited. Once the immune complexes are formed, the subsequent inflammatory process is believed to be essentially the same as that seen following deposition of preformed complexes. However, the different mode of deposition distinguishes this syndrome from typical GN caused by circulating immune complexes.

Features of blood flow and vascular structure are also important in determining the localization of immune complex deposits. Chief among these is capillary permeability. Because their capillary endothelium is fenestrated, renal glomeruli are preferential sites for the deposition of immune complexes. Hemodynamic variables enhancing immune complex localization include turbulence of flow and increased blood pressure, both of which are present in the renal glomeruli.

Complement and Complement Receptors as Regulators of Immune Complex Deposition

In addition to their proinflammatory functions, complement components can also inhibit immune complex deposition and resolubilize immune complex precipitates from sites of deposition. In addition, it is known that erythrocyte receptors for C3b, e.g., CR1, are important for reticuloendothelial clearance of opsonized circulating immune complexes.

Analysis of the clinical pattern of immune complex disease in patients with deficiencies of particular complement components provides information regarding the normal role of these components in the prevention of complex deposition. The incidence of immune complex disease in patients with deficiencies of Clq, Clr, Cls, C4, C2, or C3 varies from 60 to 90 percent, with the majority of these patients exhibiting a lupus-like syndrome. Immune complex disease is rarely associated with deficiencies of late-acting or alternative pathway components.

The binding of complement components to immune complexes prevents the formation of large antigen-antibody lattices and inhibits immune precipitation. This process requires activation via the classical pathway; serum that is deficient for Clq, C4, or C2 does not effectively inhibit lattice formation and complex precipitation. Classical pathway dependence may reflect the initial binding of C1 components, impeding the Fc—Fc interactions between IgG molecules that contribute to immune precipitation. This is followed by covalent binding of C3b to the complexes, which further inhibits immune precipitation and leads to solubilization of previously deposited complexes.

The solubilization process also depends upon activation of components of the alternative pathway. Consequently, by promoting clearance of immune complexes and inhibiting their deposition at sites of inflammation, complement components and their receptors serve as negative regulators of immune complex diseases that may retard disease development.

It should be noted that the present invention involves blocking the activities of complement component C5. The targeting of this component does not alter the functions of the early complement components, and thus does not compromise the negative regulatory effects on immune complex deposition of those early components.

Immune Complex-Mediated Inflammation

Basophils are important in the initiation of immune complex-mediated inflammatory responses, as capillary permeability is markedly increased by the action of vasoactive amines such as histamine and platelet-activating factor, which are released by these cells. Vascular permeability is also promoted by aggregation of platelets at sites of an inflammatory lesion, with the release of platelet-activating factor and the formation of microthrombi.

Basophil degranulation may reflect the effects of IgE antibodies, as well as the elaboration of the anaphylatoxin components of complement, C3a and C5a.

In addition to basophils and platelets, the primary cellular effectors of immune complex-mediated inflammation are polymorphonuclear leukocytes, monocytes, and macrophages.

IV. Previous Studies of the Role of Complement in GN Pathogenesis

Extensive work has been performed in an attempt to understand the possible role of complement in the development of GN. This work has included studies of GN using a number of animal models by, among others, Unanue, et al., (1964); Cochrane, et al., (1965); Kniker, et al., (1965); Salant, et al., (1980); Groggel, et al., (1983); Falk and Jennette (1986); Jennette, et al., (1987); Passwell, et al., (1988); Schrijver, et al., (1988); Baker, et al., (1989); Schrijver, et al., (1990); Couser, et al., (1991); and Couser, et al., (1992).

These studies have shown that complement plays a role in GN pathogenesis. However, they have not established specific unequivocal roles for the various complement components. In particular, the relative roles of C3 and other anaphylatoxins compared to the roles of the terminal complement components in GN pathogenesis have not been unequivocally established. Also, some researchers have reported that complement depletion does not diminish glomerular injury. See Kniker, et al., (1965).

The foregoing work includes that of Falk and Jennette (1986), who reported results of experiments in which attempts were made to induce GN in mice having a genetic defect that resulted in a deficiency of complement component C5. The report concludes that C5 or some terminal complement component dependent on C5 plays a role in the pathogenesis of GN.

Significantly, with regard to the present invention, Falk and Jennette in no way disclose or suggest that an antibody to C5 can be used to treat GN. Indeed, it would be counterintuitive to use an antibody to treat disease which typically involves the formation and deposition of circulating antibody-antigen immune complexes. Plainly, the creation of more circulating immune complexes would seem to be the last way to go to solve a problem that can be caused by circulating immune complexes. Yet, as demonstrated by the surprising results presented below, anti-C5 antibodies have been found to effectively block GN, even though the creation of additional circulating immune complexes is inherent in their mode of action.

Baker et al. (1989), Couser et al. (1991), and Couser et al. (1992) (hereinafter referred to collectively as the "C6" work) discuss experiments in which high levels of an anti-C6 polyclonal antibody preparation were administered to rats, following which immune complexes were formed in situ in the rats' kidneys. Significantly, with regard to the present invention, the anti-C6 antibody preparation was not administered to animals with pre-existing kidney disease, i.e., it was not used as a therapeutic treatment.

Moreover, the experimental protocol used in the C6 experiments did not involve circulating immune complexes, but rather involved complexes formed in situ. Accordingly, the experiments did not disclose or suggest the counterintuitive approach of the present invention wherein more circulating immune complexes are formed in the process of treating a disease state caused by circulating immune complexes.

Further, the anti-C6 antibody dosages used in the C6 work were too high for practical medical use. Specifically, these antibodies were used at a dosage of 1 gm/kg, a dosage which would correspond to 70 gm of antibody for a 70 kg (155 lb) individual. In contrast, the anti-C5 antibodies used in the practice of the present invention are used at concentrations at or below 0.1 gm/kg, i.e., a factor of at least ten times less than used in the C6 work. Indeed, as shown by the examples presented below, anti-C5 antibody dosages as low as 0.03 gm/kg, i.e., 33 times less than those used in the C6 work, have been found to achieve the therapeutic effects of the invention. For a 70 kg individual, this-antibody level corresponds to a dose of just 2.1 gms.

In addition to lowering dosage levels, the anti-C5 antibodies used in the practice of the present invention achieve important therapeutic effects not achieved with the anti-C6 antibodies. Specifically, the control and test animals in the C6 work exhibited both hypercellularity and narrowing of capillary lumens. In direct contrast, no such hypercellularity or narrowing of capillary lumens was seen when diseased individuals were treated with anti-C5 antibodies (see FIG. 1).

Moreover, the anti-C5 antibodies used in the present invention achieve a reduction in glomerular enlargement, thus providing a clear demonstration of the unexpectedly powerful anti-inflammatory effects of the anti-C5 antibodies used in the practice of the invention. Nowhere in the C6 work is there any disclosure or suggestion of such a powerful anti-inflammatory effect.

DESCRIPTION OF THE PREFERRED EMBODIMENTS

As discussed above, the present invention relates to the use of anti-C5 antibodies in treating patients suffering from GN. The anti-C5 antibodies are used in an amount effective to substantially reduce (e.g., reduce by at least about 50%) the cell-lysing ability of complement present in the patient's blood (the "cell-lysing ability of complement present in the patient's blood" is also referred to herein as the "serum complement activity of the patient's blood"). Reduction of the cell-lysing ability of complement present in the patient's blood can be measured by methods well known in the art such as, for example, by the chicken erythrocyte hemolysis method described below under the heading "Cell Lysis Assays."

To achieve the desired reductions, the anti-C5 antibodies can be administered in a variety of unit dosage forms. The dose will vary according to the particular antibody. For example, different antibodies may have different masses and/or affinities, and thus require different dosage levels. Antibodies prepared as Fab' fragments will also require differing dosages than the equivalent intact immunoglobulins, as they are of considerably smaller mass than intact immunoglobulins, and thus require lower dosages to reach the same molar levels in the patient's blood.

The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, and preferably between about 5 mg per kg and about 50 mg per kg per patient per treatment. In terms of plasma concentrations, the antibody concentrations are preferably in the range from about 25 $\mu$g/ml to about 500 $\mu$g/ml.

Subject to the judgement of the physician, a typical therapeutic treatment includes a series of doses, which will usually be administered concurrently with the monitoring of clinical endpoints such as BUN levels, proteinuria levels, etc., with the dosage levels adjusted as needed to achieve the desired clinical outcome. Alternatively, levels of serum complement activity available in the patient's blood are monitored using the techniques set forth below under the heading "Cell Lysis Assays" to determine if additional doses or higher or lower dosage levels of antibodies are needed, with such doses being administered as required to maintain at least about a 50% reduction, and preferably about a 95% or greater reduction of serum complement activity. Other protocols can, of course, be used if desired as determined by the physician.

Administration of the anti-C5 antibodies will generally be performed by an intravascular route, e.g., via intravenous infusion by injection. Other routes of administration may be used if desired. Formulations suitable for injection are found in *Remington's Pharmaceutical Sciences*, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

The formulations of the invention can be distributed as articles of manufacture comprising packaging material and the anti-C5 antibodies. The packaging material will include a label which indicates that the formulation is for use in the treatment of kidney disease and may specifically refer to nephritis or glomerulonephritis.

The anti-C5 antibody is preferably a monoclonal antibody, although polyclonal antibodies produced and screened by conventional techniques can also be used if desired. As discussed above, the anti-C5 antibodies must be effective in reducing the cell-lysing ability of complement present in human blood. As also discussed above, this property of the antibodies can be determined by methods well known in the art such as, for example, by the chicken erythrocyte hemolysis method described below under the heading "Cell Lysis Assays".

The anti-C5 antibodies used in the practice of the invention bind to C5 or fragments thereof, e.g., C5a or C5b. Preferably, the anti-C5 antibodies are immunoreactive against epitopes on the beta chain of purified human complement component C5 and are capable of blocking the conversion of C5 into C5a and C5b by C5 convertase. This capability can be measured using the techniques described in Wurzner, et al., *Complement Inflamm* 8:328–340, 1991. Preferably, the anti-C5 antibodies are used in an amount effective to reduce the C5 convertase activity available in the patient's blood by at least about 50%.

Hybridomas producing monoclonal antibodies reactive with complement component C5 can be obtained according to the teachings of Sims, et al., U.S. Pat. No. 5,135,916. As discussed therein, antibodies are prepared using purified components of the complement membrane attack complex as immunogens. In accordance with the present invention, complement component C5 or C5b is preferably used as the immunogen. Also in accordance with the invention, the antibodies preferably should prevent the cleavage of C5 to form C5a and C5b, thus preventing the generation of the anaphylatoxic activity associated with C5a and preventing the assembly of the membrane attack complex associated with C5b. In a particularly preferred embodiment, these anti-C5 antibodies will not impair the opsonization function associated with the activation of complement component C3 by a C3 convertase. Plasma C3 convertase activity can be measured by assaying plasma for the presence of C3a as described below under the heading "Histology." Preferably, the anti-C5 antibody produces essentially no reduction in plasma C3a levels.

General methods for the immunization of animals (in this case with C5 or C5b), isolation of polyclonal antibodies or antibody producing cells, fusion of such cells with immortal cells (e.g., myeloma cells) to generate hybridomas secreting monoclonal antibodies, screening of hybridoma supernatants for reactivity of secreted monoclonal antibodies with a desired antigen (in this case C5 or C5b), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz, et al., *Cellular Immunol.* 127:337–351, 1990; Wurzner, et al., *Complement Inflamm.* 8:328–340, 1991; and Mollnes, et al., *Scand. J. Immunol.* 28:307–312, 1988.

As used herein, the term "antibodies" refers to immunoglobulins produced in vivo, as well as those produced in vitro by a hybridoma, and antigen binding fragments (e.g., Fab' preparations) of such immunoglobulins, as well as to recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins. Publications describing methods for the preparation of such antibodies, in addition to those listed immediately above, include: Reichmann, et al., *Nature*, 332:323–327, 1988; Winter and Milstein, *Nature*, 349:293–299, 1991; Clackson, et al., *Nature*, 352:624–628, 1991; Morrison, *Annu Rev Immunol*, 10:239–265, 1992; Haber, *Immunol Rev*, 130:189–212, 1992; and Rodrigues, et al., *J Immunol*, 151:6954–6961, 1993.

Without intending to limit it in any manner, the present invention will be more fully described by the following examples. The methods and materials which are common to various of the examples are as follows.

Materials and Methods
Induction of GN in Mice

Four month old female B10.D2/nSnJ mice averaging approximately 25 gms each were obtained from the Jackson Laboratory, Bar Harbor, Me. Mice were injected with 0.1 mL daily (six days per week) of a 40 mg/mL solution of horse apoferritin (HAF), which was prepared by dilution of a saline solution of HAF (Sigma Chemical Company Catalog No. A-3641) with PBS.

Anti-C5 Monoclonal Antibodies

Monoclonal antibodies that bind to complement component C5 of the mouse were prepared by standard methods as an IgG fraction from supernatants of cultures of hybridoma BB5.1 (Frei, et al., 1987), which was obtained from Dr. Brigitta Stockinger of the National Institute for Medical Research, Mill Hill, London, England.

Histology

Kidneys were subjected to microscopic analysis using standard histochemical staining and immunofluorescence techniques. Periodic Acid Schiff (PAS) staining of $5\mu$ paraffin sections was by standard methods using a HARLECO PAS histochemical reaction set (EM Diagnostic Systems, Gibbstown, N.J., number 64945/93) according to the manufacturer's directions.

Immunofluorescence staining of $5\mu$ cryostat sections was carried out by standard methods using FITC conjugated sheep anti-mouse C3 (Biodesign International, Kennebunk, Me., Catalog No. W90280F) to detect murine complement component C3, or FITC conjugated goat anti-mouse IgG, IgA, and IgM (Zymed Laboratories, South San Francisco, Calif., Catalog No. 65-6411) to detect immune complexes.

Urine Assays

Protein and glucose levels were determined by spotting urine samples on CHEMSTRIP 2GP dipsticks (Boehringer Mannheim Diagnostics, Indianapolis, Ind., Catalog No. 200743). The detection areas of these strips change color when exposed to urine containing protein or glucose; a lack of color change indicates no detectable protein or glucose is present. The level of analyte in the urine being tested is read out by matching changed colors with color charts supplied by the manufacturer. The urine protein chart shows colors corresponding to trace, 30, 100, and 500 mg/dL.

Cell Lysis Assays

The cell-lysing ability of complement in blood can be determined using hemolytic assays that are performed as follows: Chicken erythrocytes are washed well in GVBS (Rollins, et al., *J Immunol* 144:3478–3483, 1990, Sigma Chemical Co. St. Louis, Mo., catalog No. G-6514) and resuspended to $2 \times 10^8$/mL in GVBS. Anti-chicken erythrocyte antibody (IgG fraction of anti-chicken-RBC antiserum, Intercell Technologies, Hopewell, N.J.) is added to the cells at a final concentration of 25 $\mu$g/mL and the cells are incubated for 15 min. at 23° C. The cells are washed 2× with GVBS and 5×10⁶ cells are resuspended to 30 μL in GVBS. A 100 μL volume of serum test solution is then added to yield a final reaction mixture volume of 130 μL. As used herein, reference to the serum percentage and/or serum input in these assays indicates the percent serum in the 100 μL volume of serum test solution.

For assays of mouse serum activity, the 100 μL volume of serum test solution contained 50 μL of diluted (in GVBS) mouse serum and 50 μL of human C5 deficient serum (Quidel Corporation, San Diego, Calif.). For assays of human serum activity, the serum test solution may contain up to 100% human plasma or serum, with hybridoma supernatants and/or GVBS being added to yield the 100 μL volume. For the assays used to screen hybridoma supernatants discussed below in Example 7, each 100 μL volume of serum test solution contained 50 μL of hybridoma supernatant and 50 μL of a 10% solution of human serum in GVBS, yielding a 5% human serum input.

After incubation for 30 min. at 37° C., percent hemolysis was calculated relative to a fully lysed control sample. Hemolysis was determined by spinning the cells down and measuring released hemoglobin in the supernatant as the optical density at 415 nm.

A 50% reduction in hemolysis after treatment with the anti-C5 antibodies used in the practice of the invention means that the percent hemolysis after treatment is one half of the percent hemolysis before treatment.

EXAMPLE 1

Anti-C5 Antibodies Inhibit Glomerular Inflammation and Enlargement

This example illustrates that anti-C5 antibodies will inhibit glomerular inflammation and enlargement.

The protocol for these experiments was as follows. GN-induced mice were treated with anti-C5 antibodies or with PBS as a control after 2 weeks of GN induction. Each mouse received 750 μg of anti-C5 monoclonal antibodies in PBS (30 mg/kg in a 25 gm mouse) or an equal volume of PBS alone. The amount injected was from 0.25 to 0.365 mL (the concentration of antibodies in PBS varied), which was administered by intraperitoneal injection once a day, six days a week. After an additional 2 weeks of induction and treatment, the animals were sacrificed and kidneys were harvested and prepared for histological examination as described above. Kidneys were also obtained from age-matched uninduced and untreated control mice.

Figure 1C:
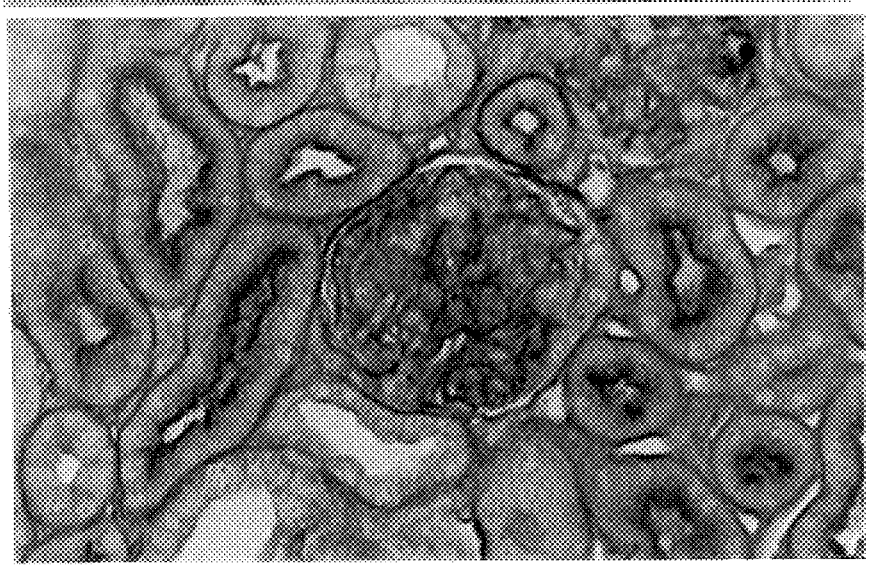

FIG. 1 shows sections of mouse kidneys with a single glomerulus located centrally amidst surrounding interstitium and cross sections of convoluted tubules in each section. As can be seen therein, the kidneys of the GN-induced, PBS-treated mice (FIG. 1B) developed severe crescentic glomerular pathology, including inflammatory glomerular hypercellularity, apparent basement membrane thickening, and glomerular enlargement, while the glomeruli of the GN-induced, anti-C5-treated animals (FIG. 1C) were essentially indistinguishable from the glomeruli of the normal healthy kidneys of the uninduced untreated mice (FIG. 1A).

Note that in the glomeruli with severe crescentic pathology, the size of the glomerular capillary network (glomerular tuft) is not enlarged, but shows signs of compression by a crescentic-shaped proliferation of epithelial cells and PAS-positive material, and the Bowman's capsule is dramatically enlarged. Also note that in the section of diseased glomerulus shown in FIG. 1B, the capillary network is split in half by a projection of the hypercellular crescentic mass.

The non-inflamed glomerulus of the uninduced untreated mouse shown in FIG. 1A is approximately 100μ in diameter; the inflamed glomerulus of the GN-induced, PBS treated mouse shown in FIG. 1B is approximately 175μ in diameter; the non-inflamed glomerulus of the GN-induced, anti-C5-treated mouse shown in FIG. 1C is approximately 90μ in diameter.

EXAMPLE 2

Anti-C5 Antibodies Prevent/Reduce Proteinuria Associated with GN

This example demonstrates that treatment with anti-C5 antibodies results in the prevention/reduction of kidney damage as evidenced by the lack of significant amounts of protein in the urine (i.e. the presence of less than 100 mg/dL of protein in the urine).

The protocol for the experiments of this example was the same as that used in the experiments of Example 1. Five PBS-treated, GN-induced mice, 6 anti-C5-treated, GN-induced mice, and 4 age-matched untreated uninduced mice were used in this study. A first set of urine samples was analyzed prior to treatment after the initial 2 week induction period. A second set of urine samples was analyzed after the 2 week treatment period. None of the untreated uninduced control animals had detectable protein in their urine at either of these timepoints.

The results obtained with the GN-induced mice are set forth in Table 1. As shown therein, at the end of the 2 week PBS treatment period, 4 out of the 5 PBS treated (control) animals developed significant proteinuria, i.e., at least 100 mg/dL of protein in the urine. The fifth animal (mouse D in Table 1) did not have detectable protein in the urine at either timepoint but, unlike the other mice in the study, was found to have very high levels of glucose in the urine after the 2 week PBS treatment period, suggesting that this animal was physiologically compromised.

In the anti-C5-treated, GN-induced group, the one mouse that developed significant proteinuria at the end of the initial 2 week induction period (mouse 6 in Table 1) improved by the end of the 2 week antibody treatment period. In addition, in contrast to the development of significant proteinuria in 4 out of 5 PBS-treated, GN-induced mice, none of the anti-C5-treated, GN-induced mice exhibited significant proteinuria at the end of the 2 week antibody treatment period.

EXAMPLE 3

Anti-C5 Antibodies Do Not Inhibit Glomerular Immune Complex Deposition

This example demonstrates that anti-C5 antibodies used in the practice of the invention achieve their therapeutic effects even though immune complexes are deposited in the glomeruli of treated animals at equivalent levels to those seen in the glomeruli of PBS-treated animals. The example further illustrates that the mechanism of operation of the anti-C5 antibodies is not through the inhibition of immune complex deposition in the glomerulus.

The protocol used in the experiments of this example was the same as that used in the experiments of Example 1. Immunofluorescence staining as described above was performed on sections from the same kidneys harvested in Example 1.

Figure 2C:
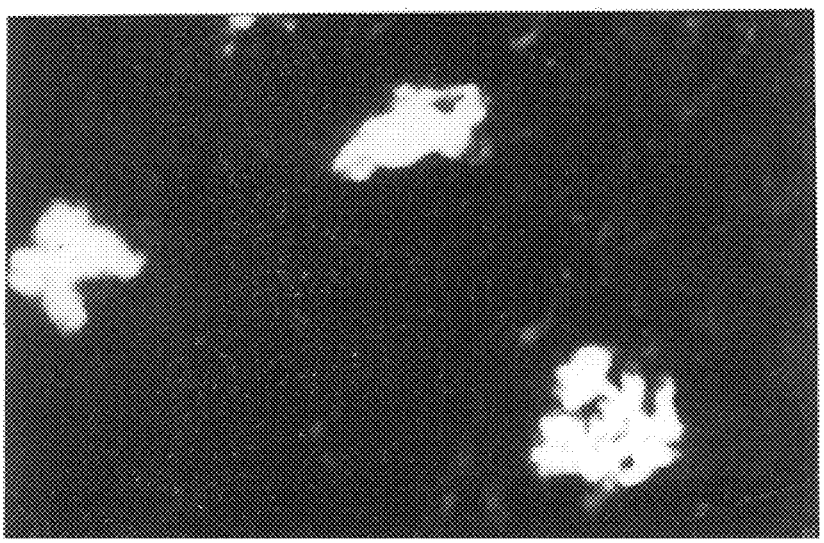

The results are shown in FIG. 2. As can be seen in this figure, equivalent amounts of immune complexes were deposited in the glomeruli of the kidneys of both the PBS-treated, GN-induced mice (FIG. 2B) and the anti-C5-treated, GN-induced mice (FIG. 2C), but not in the untreated uninduced controls (FIG. 2A). Kidneys of GN-induced mice harvested after the 2 week induction period, but before treatment, showed immune complex deposits in the glomeruli, but at lower levels (as indicated by lower fluorescence intensity) than in the kidney sections shown in FIG. 2B and FIG. 2C.

EXAMPLE 4

Anti-C5 Antibodies Inhibit C5b-9 Generation

This example demonstrates that the anti-C5 antibodies used in the practice of the invention inhibit C5b-9 generation. C5b-9 generation was assayed in 2 ways: (1) by testing the cell-lysing (hemolytic) ability of blood samples, and (2) by measuring levels of soluble C5b-9 in blood samples.

Figure 3:
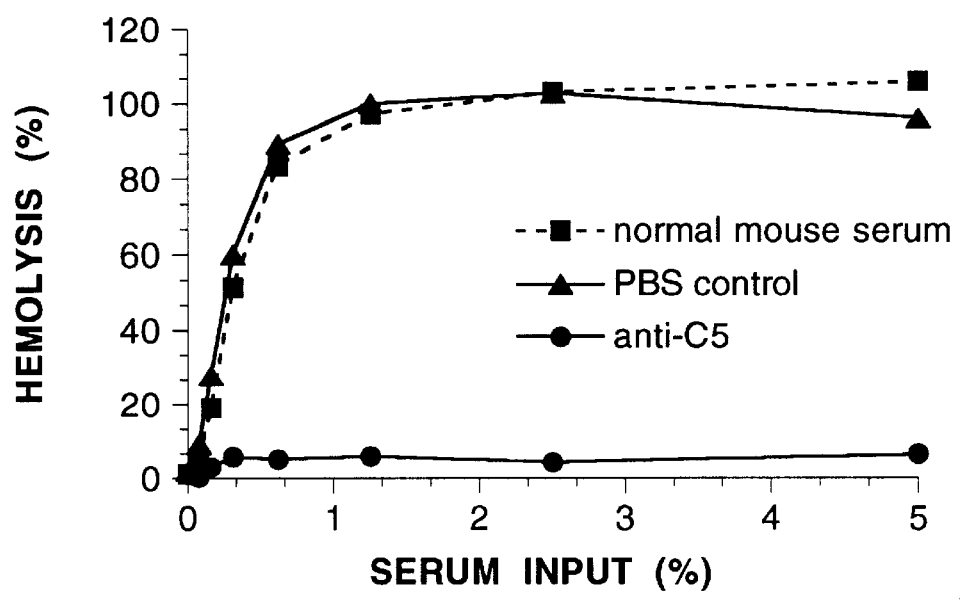
FIG. 3—Results of hemolytic (cell lysis) assays of serum from GN-induced animals treated with either anti-C5 antibodies in PBS ("Anti-C5") or PBS alone ("PBS control"). Also shown are the results of assays performed with normal serum.

FIG. 3 shows the results of cell lysis assays performed as described above, with mouse serum added to the percentage indicated on the X axis ("serum input %"). In these assays, serum from GN-induced animals treated with either anti-C5 antibodies in PBS or PBS alone (see above) was assayed at the end of the two week treatment period. Serum from normal, uninduced, uninjected mice ("normal mouse serum") obtained from Sigma Chemical Company (St. Louis, Mo., Catalog No. S-3269) was also assayed as an additional control. These results indicate that the anti-C5 monoclonal antibody administered to mice at a dosage of 30 mg/Kg completely blocked the cell lysing ability of mouse blood at serum input levels 4-fold higher than the levels of normal serum that produce maximum hemolysis in the assay.

The effects of an anti-C5 monoclonal antibody raised to human C5 was evaluated in circulating human blood. Hybridoma N19/8 (Wurzner, et al., 1991) was obtained from Dr. Otto Götze, Department of Immunology, University of Göttingen, FRG. The C5 monoclonal antibody was prepared following immunization of mice with purified human C5 protein as described in Wurzner, et al., (1991). The hybridoma was propagated in mice, and the monoclonal antibody recovered and purified as an IgG fraction from mouse ascites fluid (*Antibodies, A Laboratory Manual*, Cold Spring Harbor Laboratory, New York, 1988; *Current Protocols In Immunology*, John Wiley & Sons, New York, 1992).

To carry out these experiments, as well as others described below in Examples 5 and 6, 300 mL of whole human blood was drawn from a healthy human donor and additionally a 1 mL sample was removed as a control sample for later analysis. The blood was diluted to 600 mL by the addition of Ringer's lactate solution containing 10 U/mL heparin. The anti-C5 mAb (30 mg in sterile PBS) was added to the diluted blood to a final concentration of 50 µg/mL (results using test samples obtained in this way are labeled "+anti-C5 sample" in FIG. 4 and FIG. 6). In a control experiment, an equal volume of sterile PBS was added to diluted blood (results using control samples obtained in this way are labeled "−anti-C5 sample" in FIG. 4 and FIG. 6).

The blood was then used to prime the extracorporeal circuit of a COBE CML EXCEL membrane oxygenator cardiopulmonary bypass (CPB) machine (Cobe BCT, Inc., Lakewood, Colo.) and circulation through the circuit was started. The circuit was cooled to 28° C. and circulated for 60 minutes. The circuit was then warmed to 37° C. and circulated for an additional 30 minutes, after which time the experiment was terminated. Mechanical circulation of blood in this fashion activates the complement cascade. Samples were taken at several time points.

Figure 4:
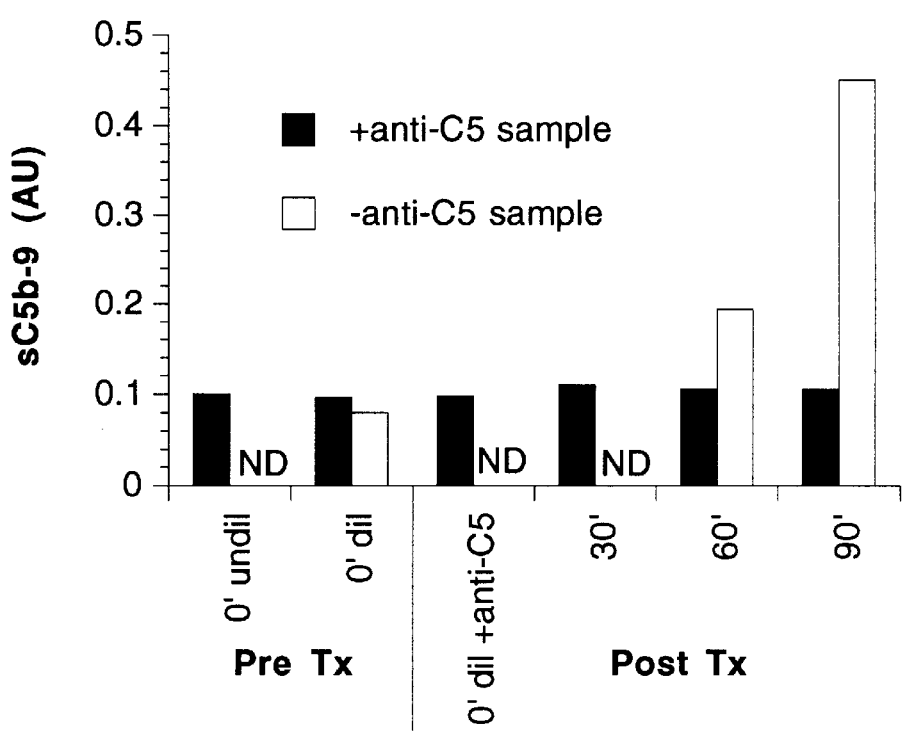
FIG. 4—Results of soluble C5b-9 ("sC5b-9") assays. "ND" indicates not determined.
Figure 6:
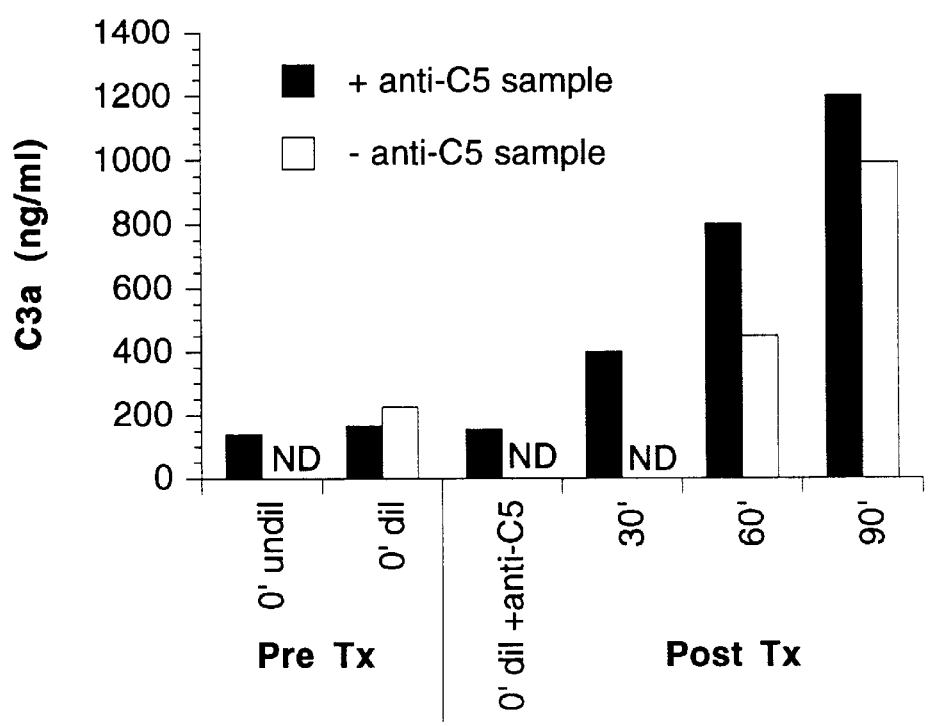
FIG. 6—Results of C3a assays of samples of circulating human blood. "ND" indicates not determined.

At each time point an aliquot of blood was taken, and subaliquots were centrifuged to remove all cells and the remaining plasma diluted 1:1 in Quidel sample preservation solution (Quidel Corporation, San Diego, Calif.) and stored at −80° C. for subsequent evaluation of soluble C5b-9 (sC5b-9) generation. Diluted subaliquots of plasma were also frozen for evaluation of C3a generation (see Example 5, below). Undiluted subaliquots of plasma were frozen at −80° C. for analysis in hemolytic assays to evaluate the pharmacokinetics of the effects of the anti-C5 antibodies on the cell lysing ability of complement present in the blood (see Example 6, below). These experiments are also discussed in copending U.S. patent application Ser. No. 08/217,391, filed Mar. 23, 1994.

sC5b-9 assays were performed before the addition of the antibody or the commencement of the CPB circuit (labeled "Pre Tx" in FIG. 4 and FIG. 6) using undiluted blood (i.e. blood from the 1 mL sample taken before the blood was diluted with Ringer's lactate solution—labeled "undil" in FIG. 4 and FIG. 6) and Ringer's lactate solution diluted blood (labeled "dil" in FIG. 4 and FIG. 6). Samples of Ringer's lactate solution diluted blood to which the antibody had been added (labeled "Post Tx" in FIG. 4 and FIG. 6) were assayed at the times indicated after starting the CPB circuit.

As can be seen in FIG. 4, while sC5b-9 levels were more than 4-fold higher in untreated samples after 90 minutes of circulation than before circulation, the anti-C5 antibody completely inhibited C5b-9 generation throughout the 90 minute time course of circulation so that sC5b-9 levels during circulation were essentially equivalent to control, uncirculated samples, at all timepoints.

EXAMPLE 5

Anti-C5 Antibodies Do Not Inhibit C3 Deposition or Activation

This example demonstrates that treatment with anti-C5 antibodies does not result in the inhibition of the activation of complement component C3 or in the deposition of C3 or its activated fragments in glomeruli.

Figure 5C:

The deposition of C3, or the fragments generated by its activation (e.g., C3a and C3b), in the glomeruli of GN-induced and GN-uninduced mice was visualized by immunofluorescence staining with a FITC-conjugated sheep anti-mouse C3 antibody preparation using standard methods, as described above. As can be seen in FIG. 5, kidneys of the PBS-treated (FIG. 5B) and the anti-C5 antibody-treated (FIG. 5C) GN-induced mice had roughly equivalent levels of C3 immunoreactive material in the glomeruli, while the uninduced untreated control mice had only traces of C3 immunoreactive material in their kidneys (FIG. 5A).

Note that the print shown in FIG. 5A was overexposed compared to those of FIG. 5B and FIG. 5C to show the very slight levels of reactivity present in normal uninduced kidneys. Kidneys of GN-induced mice harvested after the 2 week induction period, but before treatment, showed C3 immunoreactive materials in the glomeruli, but at lower levels (as indicated by lower fluorescence intensity) than in the kidney sections shown in FIG. 5B and FIG. 5C.

Anti-human C5 antibodies were also tested for possible inhibition of C3 activation in human blood prepared and circulated as described above in Example 4. Activation of complement component C3 was indicated by the presence in the blood of the C3 activation product C3a. C3a assays were performed as follows.

The plasma samples that had previously been diluted in Quidel sample preservation solution and frozen (see Example 4) were assayed for the presence of C3a by using the Quidel C3a EIA kit (Quidel Corporation, San Diego, Calif.) according to the manufacturers specifications. Concentrations of C3a in the samples is expressed as ng/well as determined by comparison to a standard curve generated from samples containing known amounts of human C3a.

As seen in FIG. 6, the addition of the anti-C5 mAb had no inhibitory effect on the production of C3a during the circulation of human blood in this experiment.

EXAMPLE 6

Pharmacokinetics of Anti-C5 Antibodies

The in vivo duration of action of mAb BB5.1, and a Fab' fragment of mAb BB5.1 (prepared by standard methods) was determined in normal female BALB/cByJ mice (averaging approximately 20 gms each) which were obtained from the Jackson Laboratory, Bar Harbor, Me. The mice were given a single intravenous injection (at 35 mg/kg body weight) of the mAB or the Fab' fragment of the mAb (or an equal volume of PBS as a control). Blood samples were collected from the retroorbital plexus at 1, 4, 24, 96, and 144 hours after administration of PBS; 4, 16, and 24 hours after administration of the Fab' fragment of mAb BB5.1; and 4, 24, 48, 72, 96, and 144 hours after administration of intact mAb BB5.1.

Figure 7A:
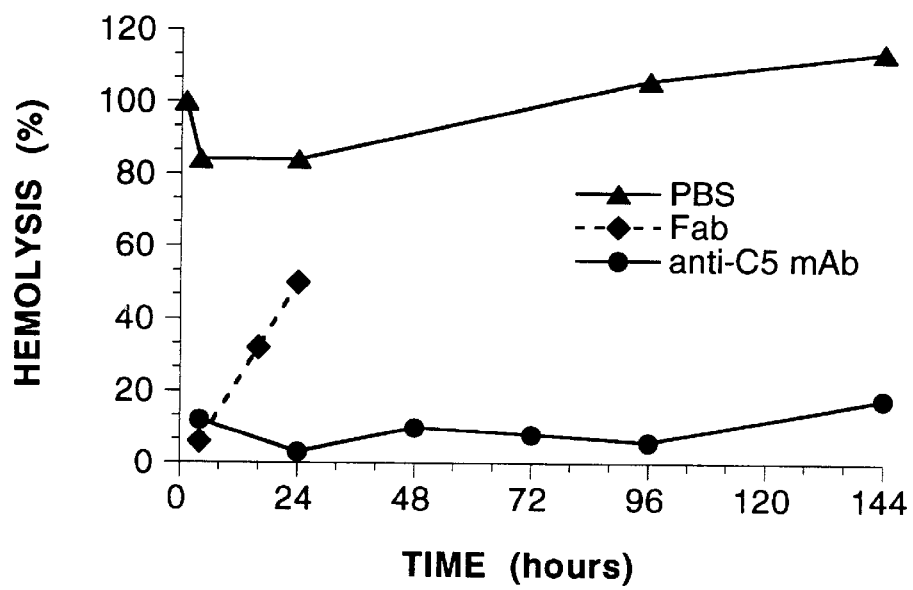
FIGS. 7A and 7B—Pharmacokinetic analyses of the reduction of the cell lysis ability of mouse (FIG. 7A) or human (FIG. 7B) blood after treatment with anti-C5 antibodies.

FIG. 7A shows the time course of inhibition of the cell-lysing ability of complement in mouse blood (determined, by testing serum obtained from the blood and diluted to 2.5%, as described above) after the in vivo administration of the mAb, the Fab' fragment, or the PBS. As shown in the figure, the mAb almost completely inhibited the hemolytic activity of the blood throughout the 6 day test period. The Fab', however, had a half-life of approximately 24 hours.

In addition to the above experiments, at the end of the 6 day testing period all of the mice were sacrificed. Kidneys, lungs, and livers were harvested and examined by gross inspection, as well as by microscopic examination of stained sections. All of the organs of the anti-C5 antibody treated animals appeared the same as those taken from PBS control treated animals. The overall appearance of the test and control mice was also indistinguishable prior to necropsy.

Figure 7B:
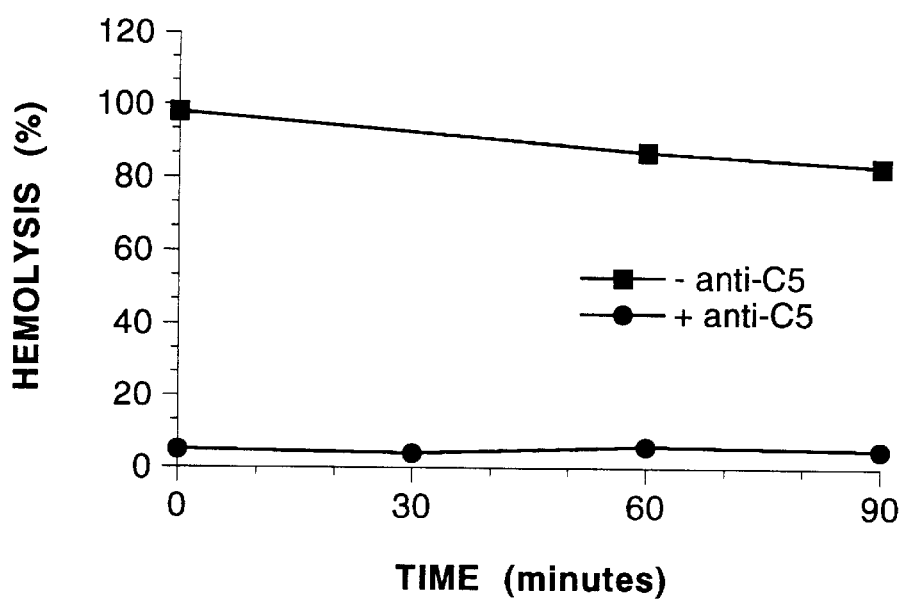

Anti-human C5 antibodies were also tested for pharmacokinetic properties in circulating human blood as described above in Example 4. As described therein, the hemolysis inhibiting effects of an anti-human C5 monoclonal antibody were assayed over a 90 minute period of circulation. The results of these assays are charted in FIG. 7B, and show that the N19/8 anti-C5 mAb essentially completely inhibited the cell lysing ability of the human blood during the entire 90 minute period of circulation.

The results of these experiments demonstrate that the anti-C5 antibodies will survive in the bloodstream for a substantial period of time, thus making periodic administration practical.

EXAMPLE 7

Preparation of Anti-C5 Monoclonal Antibodies

A monoclonal antibody suitable for use in the practice of the present invention and having the unique ability to bind to both the alpha and beta chains of the human C5 protein, was prepared in accordance with the teachings of Sims, et al., U.S. Pat. No. 5,135,916, as follows.

Balb/c mice were immunized three times by intraperitoneal injection with human C5 protein (Quidel Corporation, San Diego, Calif, Cat # A403). The first injection contained 100 µg of C5 protein in a complete Freund's adjuvant emulsion, the second immunization contained 100 µg of C5 protein in an incomplete Freund's adjuvant emulsion, and the third immunization was 100 µg of protein in PBS. The mice were injected at roughly 2 month intervals.

Fusions of splenocytes to myeloma cells to generate hybridomas were performed essentially as described in Current Protocols in Immunology (John Wiley & Sons, New York, 1992, pages 2.5.1 to 2.5.17). One day prior to fusion the mice were boosted IV with 100 µg of C5 protein. On the day of fusion, the immunized mice were sacrificed and spleens was harvested. SP2/0-AG14 myeloma cells (ATCC CRL#1581) were used as the fusion partner. SP2/0-AG14 cultures were split on the day before the fusion to induce active cell division. A ratio of 1:10 (myeloma cells:splenocytes) was used in the fusions.

The cells were fused using PEG 1450 in PBS without calcium (Sigma Chemical Company, St. Louis, Mo., Catalog No. P-7181) and plated at $1$–$2.5 \times 10^5$ cells per well. Selection in EX-CELL 300 medium (JRH Biosciences, Lexena, Kans., Catalog No. 14337-78P) supplemented with 10% heat inactivated fetal bovine serum (FBS); glutamine, penicillin and streptomycin (GPS); and HAT (Sigma Chemical Company, St. Louis, Mo., Catalog No. H-0262) was started the following day. The fusions were then fed every other day with fresh FBS, GPS, and HAT supplemented medium. Cell death could be seen as early as 2 days and viable cell clusters could be seen as early as 5 days after initiating selection. After two weeks of selection in HAT, surviving hybridomas chosen for further study were transferred to EX-CELL 300 medium supplemented with FBS, GPS, and HT (Sigma Chemical Company, St. Louis, Mo., Catalog No. H-0137) for 1 week and then cultured in EX-CELL 300 medium supplemented with FBS and GPS.

Hybridomas were screened for reactivity to C5 and inhibition of complement-mediated hemolysis 10–14 days after fusion, and were carried at least until the screening results were analyzed. The screen for inhibition of hemolysis was the chicken erythrocyte lysis assay described above. The screen for C5 reactivity was an ELISA, which was carried out using the following protocol:

A 50 µL aliquot of a 2 µg/mL solution of C5 (Quidel Corporation, San Diego, Calif.) in sodium carbonate/ bicarbonate buffer, pH 9.5, was incubated overnight at 4° C. in each test well of a 96 well plate (Nunc-Immuno F96 Polysorp, A/S Nunc, Roskilde, Denmark). The wells were then subjected to a wash step. (Each wash step consisted of three washes with TBST.) Next, test wells were blocked with 200 µL of blocking solution, 1% BSA in TBS (BSA/TBS), for 1 hour at 37° C. After an additional wash step, a 50 µL aliquot of hybridoma supernatant was incubated in each test well for 1 hour at 37° C. with a subsequent wash step. As a secondary (detection) antibody, 50 µL of a 1:2000 dilution of horseradish peroxidase (HRP) conjugated goat anti-mouse IgG in BSA/TBS, was incubated in each test well for 1 hour at 37° C., followed by a wash step. Following the manufacturer's procedures, 10 mg of O-phenylenediamine (Sigma Chemical Company, St. Louis, Mo., Catalog No. P-8287) was dissolved in 25 mLs of phosphate-citrate buffer (Sigma Chemical Company, St. Louis, Mo., Catalog No.

P-4922), and 50 μL of this substrate solution was added to each well to allow detection of peroxidase activity. Finally, to stop the peroxidase detection reaction, a 50 μL aliquot of 3N hydrochloric acid was added to each well. The presence of antibodies reactive with C5 in the hybridoma supernatants was read out by a spectrophotometric OD determination at 490 nm.

The supernatant from a hybridoma designated as 5G1.1 tested positive by ELISA and substantially reduced the cell-lysing ability of complement present in normal human blood in the chicken erythrocyte hemolysis assay. Further analyses revealed that the 5G1.1 antibody has two surprising properties: 1) it reduces the cell-lysing ability of complement present in normal human blood so efficiently that, even when present at roughly one-half the molar concentration of human C5 in the hemolytic assay, it can almost completely neutralize serum hemolytic activity; and 2) it binds to both the alpha and beta chains of the human C5 protein.

The surprising and unanticipated ability of the monoclonal antibody produced by hybridoma 5G1.1 (the 5G1.1 mAb) to bind to both the alpha and beta chains of the human C5 protein was revealed when immunoblot analysis was undertaken to further characterize the 5G1.1 mAb. Human C5 (Quidel Corporation, San Diego, Calif., Catalog No. A403) was subjected to polyacrylamide gel electrophoresis under reducing conditions, transferred to a nitrocellulose membrane, and probed with the 5G1.1 mAb as a purified IgG preparation. Two bands were immunoreactive with the 5G1.1 mAb at apparent molecular weights corresponding to those of the alpha and beta chains of the human C5 protein.

Hybridoma 5G1.1 was deposited with the American Type Culture Collection, 12301 Parklawn Drive, Rockville, Md., 20852, United States of America, on Apr. 27, 1994, and has been assigned the designation HB-11625. This deposit were made under the Budapest Treaty on the International Recognition of the Deposit of Micro-organisms for the Purposes of Patent Procedure (1977).

Throughout this application various publications and patent disclosures are referred to. The teachings and disclosures thereof, in their entireties, are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

REFERENCES

Baker, et al., 1989, *American Journal of Pathology.* 135, pp. 185–194.
Clackson, et al., 1991, *Nature.* 352, pp. 624–628.
Cochrane, et al., 1965, *Journal of Experimental Medicine.* 122, pp. 99–116.
Coligan, et al., eds. 1992, *Current Protocols in Immunology.* John Wiley & Sons, New York.
Couser, et al., 1985, *Kidney International.* 28, pp. 897–890.
Couser, et al., 1991, *Journal of the American Society of Nephrology.* 2, pp. 894–901.
Couser, 1992, in *Cecil Textbook of Medicine,* 19th Ed. (Wyngaarden, Smith, and Bennett, eds.) W. B. Saunders Co., Philadelphia, Pa., Ch. 79, pp. 551–568.
Couser, et al., 19920, *Nephrology Dialysis Transplantation.* Suppl. 1, pp. 25–30.
Couser, 1993, *Kidney International.* 44, Suppl. 42, pp. S19–S26.
Falk and Jennette, 1986, *Kidney International.* 30, pp. 678–686.
Fearon, 1983, in *Intensive Review of Internal Medicine,* 2nd Ed. Fanta and Minaker, eds. Brigham and Women's and Beth Israel Hospitals, pp. 204–210.
Floege, et al., 1992, *Laboratory Investigation.* 67, pp. 486–497.
Frei, et al., 1987, *Molecular and Cellular Probes.* 1, pp. 141–149.
Glassock and Brenner, 1987, in *Harrison's Principles of Internal Medicine.* 11th Ed. (Braunwald, Isselbacher, Petersdorf, Wilson, Martin, and Fauci, eds.) McGraw-Hill Book Co., New York, N.Y., Ch. 222 & 223, pp. 1170–1189.
Glassock and Brenner, 1994, in *Harrison's Principles of Internal Medicine,* 13th Ed. (Isselbacher, Braunwald, Wilson, Martin, Fauci, and Kasper, eds.) McGraw-Hill, Inc., New York, N.Y., pp. 1292–1313.
Groggel, et al., 1983, *Journal of Clinical Investigations.* 72, pp. 1948–1957.
Guyton, 1971, *Textbook of Medical Physiology,* 4th Ed. W. B. Saunders Co., Ch. 34 & 38, pp. 393–405 & pp. 442–454.
Haber, 1992, *Immunology Review.* 130, pp. 189–212.
Harlow and Lane, 1988, *Antibodies. A Laboratory Manual,* Cold Spring Harbor Laboratory, New York.
Jennette, et al., 1987, *American Journal of Pathology.* 127, pp. 499–506.
Knicker and Cochrane, 1965, *Journal of Experimental Medicine.* 122, pp. 83–98.
Liddell and Cryer, 1991, *A Practical Guide to Monoclonal Antibodies,* John Wiley & Sons, Chichester, West Sussex, England.
Mollnes, et al., 1988, *Scandinavian Journal of Immunology.* 28, pp. 307–312.
Montz, et al., 1990, *Cellular Immunoloqy.* 127, pp. 337–351.
Morrison, et al., 1992, *Annual Review of Immunology.* 10, pp. 239–265.
Passwell, et al., 1988, *The American Society for Clinical Investigation,* Inc. 82, pp. 1676–1684.
Reichmann, et al., 1988, *Nature.* 332, pp. 323–327.
*Remington's Pharmaceutical Sciences,* 17th Ed. 1985, Mack Publishing Company, Philadelphia, Pa.
Rich, 1992, in *Cecil Textbook of Medicine,* 19th Ed. (Wyngaarden, Smith, and Bennett, eds.) W. B. Saunders Co., Philadelphia, Pa., Ch. 249, pp. 1467–1470.
Robbins and Cotran, 1979, *Pathologic Basis of Disease.* 2nd ed. W. B. Saunders Co., Philadelphia, Pa., pp. 1128–1129.
Rodrigues, et al., 1993, *Journal of Immunology.* 151, pp. 6954–6961.
Salant, et al., 1980, *Journal of Clinical Investigations.* 66, pp. 1339–1350.
Schrijver, et al., 1988, *Laboratory Investigation.* 59, pp. 484–491.
Schrijver, et al., 1990, *Kidney International.* 38, pp. 86–95.
Unanue and Dixon, 1964, *Journal of Experimental Medicine.* 119, pp. 965–982.
Winter and Milstein, 1991, *Nature.* 349, 293–299.
Wurzner, et al., 1991, *Complement Inflammation.* 8, 328–340.

TABLE 1

Prevention/Reduction of Proteinuria by Treatment With Anti-C5 Antibodies

| | Before Treatment Urine Protein (mg/dL) | After Treatment Urine Protein (mg/dL) |
|---|---|---|
| PBS Control | | |
| mouse A | none | 100 |
| mouse B | none | 500 |
| mouse C | none | 500 |

TABLE 1-continued

Prevention/Reduction of Proteinuria by Treatment
With Anti-C5 Antibodies

|  | Before Treatment Urine Protein (mg/dL) | After Treatment Urine Protein (mg/dL) |
|---|---|---|
| mouse D* | trace | trace |
| mouse E | 100 | 100 |
| Anti-C5 Treated |  |  |
| mouse 1 | none | none |
| mouse 2 | none | 30 |
| mouse 3 | 30 | trace |
| mouse 4 | 30 | 30 |
| mouse 5 | 30 | 30 |
| mouse 6 | 100 | 30 |

*Mouse D had more than 500 mg/dL urine glucose after treatment

What is claimed is:

1. A method for the treatment of pre-existing glomerulonephritis in a patient in need of such treatment comprising introducing an antibody specific to complement component C5 into the patient's bloodstream in an amount effective to substantially reduce the cell-lysing ability of complement present in the patient's blood.

2. The method of claim 1 wherein the antibody reduces the conversion of complement component C5 into complement components C5a and C5b.

3. The method of claim 1 wherein the antibody binds to C5b.

4. The method of claim 1 wherein the antibody does not substantially inhibit formation of complement component C3b.

5. The method of claim 1 wherein the antibody is introduced into the patient's bloodstream in a dose that is not greater than 0.1 grams per kilogram.

* * * * *